US006901147B1

(12) United States Patent
Enamito et al.

(10) Patent No.: US 6,901,147 B1
(45) Date of Patent: May 31, 2005

(54) THREE-DIMENSION ACTIVE SILENCER

(75) Inventors: Akihiko Enamito, Kawasaki (JP); Takuro Hayashi, Yokohama (JP); Kunio Matsukura, Kawasaki (JP); Satoshi Aoyagi, Yokohama (JP); Tsutomu Shioyama, Yokohama (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 717 days.

(21) Appl. No.: 09/604,904

(22) Filed: Jun. 28, 2000

(30) Foreign Application Priority Data

Jun. 29, 1999 (JP) .......................................... 11-184232

(51) Int. Cl.[7] ................................................ A61F 11/06
(52) U.S. Cl. ...................................... 381/71.4; 381/71.5
(58) Field of Search ................................ 381/71.4, 71.5

(56) References Cited

U.S. PATENT DOCUMENTS 5,478,199 A * 12/1995 Gliebe ........................ 415/119
5,535,283 A * 7/1996 Saruta et al. .............. 381/71.5
6,192,133 B1 * 2/2001 Enamito et al. ........... 381/71.5

FOREIGN PATENT DOCUMENTS

JP 05-231706 9/1993
JP 07134590 A * 5/1995 ............. F01N/1/00

OTHER PUBLICATIONS

K. Kido, et al., Transactions of the ASME, vol. 111, pps. 480–485, "Active Reduction of Noise by Additional Noise Source and its Limit," Oct. 1989.

P.A. Nelson, et al., Journal of Sound and Vibration, vol. 116, No. 3, pps. 397–413, "The Minimum Power Output of Free Field Point Sources and the Active Control of Sound," 1987.

P.A. Nelson, et al., Journal of Sound and Vibration, vol. 117, No. 1, pps. 1–13, "The Active Minimization of Harmonic Enclosed Sound Fields, Part I: Theory," 1987.

* cited by examiner

*Primary Examiner*—Forester W. Isen
*Assistant Examiner*—Devona E. Faulk
(74) *Attorney, Agent, or Firm*—Oblon, Spivak, McClelland, Maier & Neustadt, P.C.

(57) ABSTRACT

A three-dimension active silencer includes a measuring unit for detecting a signal relating to a sound radiated from a target sound source which is located in a closed box. A plurality of additional sound sources are arranged around the target sound source. A microphone is arranged at a predetermined position for detecting a sound power at the position. A controller is adapted to control respective amplitudes of the additional sound sources which can be different from an amplitude of the target sound source and respective phases of the additional sound sources, based on the signal detected by the measuring unit, in such a manner that the microphone detects the lowest sound power. The additional sound sources are arranged in such a manner that a position $x_p$ of the target sound source, respective relative positions $d_i$ (i=1, 2, . . . , N) of the N additional sound sources from the target sound source and a wave number k of the sound radiated from the target sound source can substantially satisfy the following expression.

$$\frac{1}{N}\sum_{i=1}^{N} \cos k(x_p - d_i) - \cos k \cdot x_p \cong 0$$

According to the feature, it can be achieved to reduce the total sound power in the closed box including the target sound source.

4 Claims, 13 Drawing Sheets

THREE-DIMENSION ACTIVE SILENCER

FIELD OF THE INVENTION

This invention relates to a silencer for reducing a sound power radiated from a machine, in particular, to a three-dimension active silencer that is suitable for reducing a sound power radiated from a machine such as a generator in a three-dimension space.

BACKGROUND OF THE INVENTION

There is known an active silencer for a sound transmitted in a one-dimensional manner such as a sound radiated from an exhaust duct of a generator engine. The active silencer is called a one-dimension active silencer, and used in many fields.

FIG. 21 is a schematic view of a conventional one-dimension active silencer. As shown in FIG. 21, in opposition to a sound transmitted from a sound source 52 arranged at an end of the exhaust duct 51, the conventional one-dimension active silencer 50 is intended to reduce a sound power at an outlet 53, which is the other end of the exhaust duct 51, to zero.

The one-dimension active silencer 50 has a microphone 54 arranged at a side of the sound source 52 in the exhaust duct 51 in order to detect a sound signal in the exhaust duct 51. The one-dimension active silencer 50 has also a similar microphone 55 arranged at a side of the outlet 53 in the exhaust duct 51 in order to detect a sound signal in the exhaust duct 51.

A speaker 56 which can generate an additional sound is provided between the two microphones 54 and 55 in the exhaust duct 51. An adaptation controller 57 is provided for controlling the speaker 56. The adaptation controller 57 is adapted to control the speaker 56 based on a Filtered-X LMS algorithm, which is often used in general adaptation controlling systems.

The adaptation controller 57 has a compensation filter 58 for a transmitting function, a fixed FIR (Finite Impulse Response) filter 59 and an adaptive FIR filter 60. An output signal from the microphone 54 is adapted to be inputted to the compensation filter 58 and the fixed FIR filter 59. An output signal from the microphone 55 is adapted to be inputted to the adaptive FIR filter 60. An output from the fixed FIR filter 59 is adapted to be inputted to the speaker 56. Then, the adaptation controller 57 is adapted to automatically determine controlling coefficients in such a manner that the sound level detected by the microphone 55 is substantially zero.

In such a one-dimension active silencer 50, based on the sound detected by the microphone 54, the speaker 56 generates an additional sound having a reverse phase with respect to the detected sound. Thus, the additional sound interferes with the sound transmitted from the sound source 52 in the exhaust duct 51. The result of the interference is monitored by the microphone 55. Then, the speaker 56 continues to be controlled to generate an additional sound in such a manner that the sound power is reduced to substantially zero at the position where the microphone 55 is arranged. Once the sound power is reduced to zero at a position, the position reflects the sound because of difference in sound impedance. Therefore, the sound is not transmitted to the outlet 53 any more.

As described above, the one-dimension active silencer 50 cause the sound power from the sound source to interfere with the additional sound and to reduce to substantially zero when the sound power is transmitted in a one-dimensional manner, for example when the sound power is transmitted through the exhaust duct 51. However, the one-dimension active silencer 50 is not effective in reducing a sound power transmitted in a three-dimensional manner.

There is known a method for reducing a total acoustic power when a sound power from a sound source such as a machine is radiated to a three-dimension space. In the method, many additional sound sources are arranged around the sound source. The respective additional sound sources generate respective additional sounds in order to reduce a sound power leaked from a space surrounded by the additional sound sources as much as possible. Such a conventional three-dimension active silencer is schematically shown in FIG. 22.

As shown in FIG. 22, a plurality of additional sound sources 113 are arranged on a surrounding spherical surface 112 around a machine 111 as a target sound source. A plurality of microphone 114 is arranged close to the plurality of additional sound sources 113, respectively.

Each of the plurality of microphones 114 is connected to a common controller 115 which is adapted to drive and control the plurality of additional sound sources 113. A reference signal relating to a sound radiated from the machine 111, for example a vibration signal of an engine if the machine 111 is the engine, is adapted to be inputted into the controller 115.

The controller 115 conducts a control based on the reference signal in such a manner that each of the sound levels detected by the microphones 114 is reduced to a substantially minimum, respectively. That is, the controller 115 determines an amplitude and a phase of each of the additional sound sources 113 in such a manner that a sum of squares of the sound levels detected by the microphones 114 is a minimum.

However, in the silencer system shown in FIG. 22, each of the microphones 114 detects a plurality of additional sounds radiated from the plurality of additional sound sources 113, at the same time (multi-overlapping). Thus, a controlling system in the controller 115 has to be built considering an affect of the multi-overlapping, which makes the controlling system more complex. In addition, a gap between each neighboring two of the additional sound sources 113 has to be less than half a wavelength of the sound from the target sound source. Thus, if the spherical surface 112 is defined far from the machine (target sound source) 111, the number of the additional sound sources 113 has to be increased.

In addition, although the conventional active silencing control can achieve lowest sound powers at the positions where the microphones 114 are placed, it does not necessarily mean that a total acoustic power is a substantially minimum. That is, it is still not achieved to control to reduce a total acoustic power in a three-dimension space including a machine as a sound source.

On the other hand, there are known some passive silencing controls such as sound absorption or sound shading. However, the passive silencing controls is not so effective, especially when a main component of the sound is a low tone for example when the sound is radiated from a generator.

SUMMARY OF THE INVENTION

The object of this invention is to solve the above problems, that is, to provide a three-dimension active silencer that has a simpler controlling system and that is more effective.

In order to achieve the object, a three-dimension active silencer, comprises: a measuring unit configured to detect a signal relating to a sound radiated from a target sound source which is located in a closed box; a plurality of additional sound sources arranged around the target sound source; a microphone arranged at a predetermined position for detecting a sound level at the position; and a controller configured to control respective amplitudes of the additional sound sources which can be different from an amplitude of the target sound source and respective phases of the additional sound sources, based on the signal detected by the measuring unit, in such a manner that the microphone detects the lowest sound level; wherein the additional sound sources are arranged in such a manner that a position xp of the target sound source, respective relative positions $d_i$ (i =1, 2, . . . , N) of the N additional sound sources from the target sound source and a wave number k of the sound radiated from the target sound source can substantially satisfy a relationship:

$$\frac{1}{N}\sum_{i=1}^{N}\cos k(x_p-d_i)-\cos k\cdot x_p\cong 0$$

According to the feature, since the N additional sound sources are arranged in such a manner that the above expression is satisfied, a total acoustic power can be reduced to a minimum. As a result, it can be achieved to reduce the total acoustic power in the closed box (a three-dimension space) including the target sound source.

The above silencer is effective, especially when a main component of the sound is a low tone for example when the sound is radiated from an engine in a generator box or an exhaust duct. However, the above silencer is also effective against a target sound not in a closed box such as an engine for a small generator.

The signal detected by the measuring unit may be an accelerating signal obtained from a surface of an engine or the like, a rotating pulse signal, or an AC output signal produced by a generator.

Form many simulation experiments, it is found that the microphone is preferably arranged at a position within one fourth of a wavelength of the sound from the target sound source.

Preferably, the controller has a digital controlling part including a controlling-coefficient calculator which calculate controlling coefficients and a controlling-coefficient processor which calculate sum of products of the controlling coefficients and the signal, and the controlling coefficients are updated substantially every moment.

Preferably, the controller has: an analogue controlling part including a first band-pass filter, a phase adjuster and an amplitude adjuster; and an acoustic-power monitoring part including a second band-pass filter, an AD/DA converter and a digital circuit.

Preferably, the microphone is arranged in an area which is not in a node area of the sound radiated from the target sound source and which is not in node areas of sounds radiated from the additional sound sources.

In addition, a three-dimension active silencer for both a first target sound source and a second target sound source, comprises: a first additional sound source arranged around the first target sound source; second additional sound source arranged around the second target sound source; a first microphone arranged at a first predetermined position for detecting a sound level at the first position; a second microphone arranged at a second predetermined position close to the second target sound source for detecting a sound level at the second position; a second controller configured to control respective amplitudes of the second additional sound sources and respective phases of the second additional sound sources, in such a manner that the second microphone detects the lowest sound level; and a first controller configured to control respective amplitudes of the first additional sound sources and respective phases of the first additional sound sources, in such a manner that the first microphone detects the lowest sound level.

In the case, preferably, a distance between the second position where the second microphone is arranged and the second target sound source is substantially equal to a distance between the second position and the second additional sound source. More preferably, the second position where the second microphone arranged is substantially intermediate between the second target sound source and the second additional sound source.

Preferably, a plurality of second additional sound sources are arranged around the second target sound source, and a volume velocity of the second target sound source is substantially equal to a sum of respective volume velocities of the plurality of second additional sound sources.

The silencer having the above feature is effective especially when a sound radiated from the second target sound source has a substantially same frequency, a delayed amplitude and a delayed phase, with respect to a sound radiated from the first target sound source.

BEST MODE FOR CARRYING OUT THE INVENTION

Embodiments of the invention will now be described in more detail with reference to drawings.

First Embodiment

Figure 1:
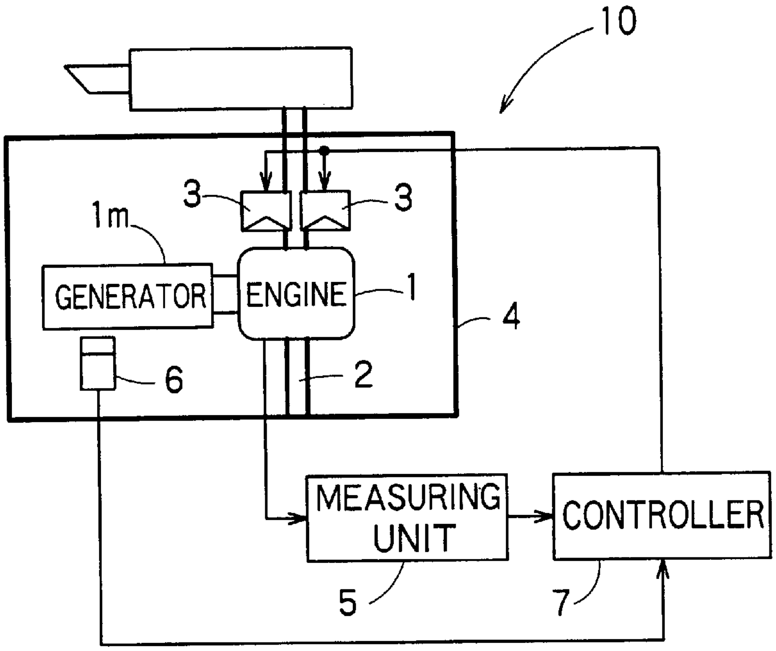
FIG. 1 is a schematic view of a first embodiment of a three-dimension active silencer according to the invention.

FIG. 1 is a schematic view of a first embodiment of a three-dimension active silencer according to the invention. As shown in FIG. 1, the three-dimension active silencer of the first embodiment 10 is set for canceling sounds from an engine 1 and an exhaust duct 2 located in a closed box 4. In the case, the engine 1 and the exhaust duct 2 form a target sound source.

The engine 1 is connected to a generator 1*m*, and they form a private electric generator. The private electric generator is surrounded by a closed box 4. A capacity of the private electric generator is valuable from a several kVA to a thousand kVA by changing a type of engine. In the embodiment, the private electric generator has a capacity of 60 kVA. The engine 1 is a type of 4-cylinder and 4-cycle (3000 rpm). In the case, a basic frequency of an engine sound is 100 Hz. Peaks of 103 Hz and 206 Hz are actually measured.

The three-dimension active silencer 10 includes a measuring unit 5 for detecting an accelerating signal of a surface of the engine 1 as a signal relating to the sound radiated from the target sound source. In addition, N (two in FIG. 1) additional sound sources are arranged around the engine 1 as the target sound source. In the case, the additional sound sources are speakers 3. A microphone 6 is arranged at a predetermined position in the closed box 4, for detecting a sound level at the position.

The additional sound sources 3, the measuring unit 5 and the microphone 6 are connected to a common controller (controlling circuit) 7. The controller 7 is adapted to control respective amplitudes of the additional sound sources 3 which can be different from an amplitude of the target sound source 1 and respective phases of the additional sound sources 3, based on the signal detected by the measuring unit 5, in such a manner that the microphone 6 detects the lowest sound level.

The additional sound sources 3 are arranged in such a manner that a sound-center position $x_p$ of the engine 1 and the duct 2 as the target sound source, respective relative positions $d_i$ (i =1, 2, . . . , N) of the N additional sound sources from the sound-center position (the target sound source) and a wave number k of the sound radiated from the target sound source can substantially satisfy a following relationship.

$$\frac{1}{N}\sum_{i=1}^{N}\cos k(x_p - d_i) - \cos k\cdot x_p \cong 0$$

Then, an operation of the first embodiment is explained.

When the engine 1 is driven, the signal relating to the engine sound is detected by the measuring unit 5 and is inputted into the controller 7. The controller 7 adjusts the respective amplitudes and the respective phases of the additional sound sources 3, based on the signal detected by the measuring unit 5, in such a manner that the sound level detected by the microphone 6 is reduced to a minimum.

According to the above control by the controller 7, the sound power at the position where the microphone 6 is arranged can be reduced. However, since the microphone is fixed to the position, the above control may not always achieve that a total acoustic power in the closed box 4 is reduced to a minimum. In order to reduce the total acoustic power to the minimum, it is important where the additional sound sources 3 and the microphone 6 are arranged. In the embodiment, the additional sound sources 3 are arranged with a special condition in order to reduce the total acoustic power in the closed box 4 to the minimum.

The special condition about an arrangement of the additional sound sources 3 is explained below.

At first, in the embodiment, the sound power is locally high at a cylinder section in the engine 1. Thus, the target sound is radiated from the cylinder section in the same phase. That is, it is allowed to assume that the target sound source is a point sound source. Therefore, the engine sound can be treated by using a sound model that has a closed generator box (space) 4 and a point sound source therein.

When one target sound source 1 and N additional sound sources 3 are arranged in a closed space (all sound sources are point sound sources), a total acoustic power in the closed space is expressed by the following expression.

$$W = \frac{1}{2}Re\left\{p(x_p)q_p^* + \sum_{i=1}^{N}p(x_{si})q_{si}^*\right\} = \frac{\omega^2\rho c^2}{2V}\sum_r\left[\frac{2\xi_r\omega_r}{M_r\{(\omega_r^2-\omega^2)+(2\xi_r\omega_r\omega)^2\}}\times\left\{|q_p|^2\{\phi_r(x_p)\}^2 + |q_{si}|^2\sum_{i=1}^{N}\sum_{j=1}^{N}\phi_r(x_{si})\phi_r(x_{sj}) + 2|q_{si}q_p|\sum_{i=1}^{N}\phi_r(x_p)\phi_r(x_{si})\cos(\theta_{si}-\theta_p)\right\}\right] \tag{1}$$

In the above expression (1), xp represents a position of the target sound source, $\theta_p$ a phase of the target sound source, $q_p$ an amplitude of the target sound source, $x_{si}$ positions of the additional sound sources, $\theta_{si}$ phases of the additional sound sources, and $q_{si}$ amplitudes of the additional sound sources (i =1, 2, . . . , N). In addition, ω represents an angular frequency, ρ a density, C a sound velocity, V a volume of the closed space, $M_r$ a modal mass, $\xi_r$ a modal damping, $\omega_r$ an characteristic angular frequency, and $\phi_r$ ( ) a mode function.

As seen in the expression (1), the total acoustic power changes dependently on the positions $x_{si}$ the phases $\theta_{si}$ and the amplitudes $q_{si}$ of the additional sound sources 3.

A microphone 6 is arranged in the closed space. Then, the controller 7 conducts an adaptation control (Filtered-X) to reduce a sound level detected by the microphone 6 to a minimum. The controlled situation is expressed by the following expression.

$$P(x_m)=[_p, Z_{s1}, \ldots, Z_{SN}][q_p, q_{s1}, q_{SN}]^T=0 \quad (2)$$

In the above expression (2), P represents a sound level and $x_m$ a position of the microphone. In addition, Z represent terms (functions) representing transmissions from the target sound source and the additional sound sources to the microphone, respectively. In addition, q represents a sound intensity (amplitude). Respective additional characters p and si represent the target sound source 1 and an i-th (i-listed) additional sound source 3.

Then, it is assumed that the N additional sound sources 3 generate additional sounds having the same sound intensity by means of a common controlling system. The assumptions is expressed by the following expression.

$$q_{si}=q_s (i=1, 2, \ldots, N)$$

At that time, a ratio of the sound intensities between the target sound source 1 and the additional sound sources 3 ($q_s/q_p$) is expressed by the following expression.

$$\frac{q_s}{q_s} = -\frac{\dfrac{j\omega\rho c^2}{V}\sum_r \dfrac{1}{Mr}\cdot\dfrac{\phi_r(x_m)\phi_r(x_p)}{\omega_r^2-\omega^2+2j\xi_r\omega_r\omega}}{\dfrac{j\omega\rho c^2}{V}\sum \dfrac{1}{Mr}\cdot\dfrac{\phi_r(x_m)\sum_{i=1}^{N}\phi_r(x_{si})}{\omega_r^2-\omega^2+2j\xi_r\omega_r\omega}} \quad (4)$$

When the relationship is substituted into the above expression (1), the total acoustic power under the adaptation control can be obtained.

Herein, if the additional sound sources 3 have a common amplitude and a common phase reverse to the target sound source, that is, if the N additional sound sources 3 satisfies the following expression (The amplitude is 1/N and the phase is anti-phase. The $e^{j\pi}$ means -1.), it is known that the total acoustic power can be considerably reduced if a frequency of the sound is not more than 200 Hz.

$$\frac{q_s}{q_p} = \frac{1}{N}e^{j\pi} \quad (5)$$

When the relationship of the expression (5) is substituted into the above expression (4), the following relationship can be obtained.

$$\frac{1}{N}\sum_{i=1}^{N}\phi_r(x_{si}) - \phi_r'(x_p) = 0 \quad (6)$$

Herein, in the first embodiment, a mode function (characteristic mode) in the closed box 4 may be expressed by the following expression.

$\theta_r(x)$=cos k x+tm (7)

In addition, since the N additional sound sources 3 have a common amplitude and a common phase, if their relative positions with respect to the target sound source 1 (point sound source) are represented by $d_i$ $_{(i=}$1, 2, . . . , N), the following relationship can be obtained from the expressions (6) and (7). It is confirmed that the relationship is satisfied for example if $|d_i| \leqq 1/k = \alpha/2\pi$.

$$\frac{1}{N}\sum_{i=1}^{N}\cos k(x_p-d_i) - \cos k\cdot x_p \cong 0 \quad (8)$$

As described above, if the N additional sound sources 3 are arranged in such a manner that the expression (8) is satisfied, the total acoustic power in the closed box 4 can be reduced to a minimum. That is, according to the embodiment, the total acoustic power can be reduced to the minimum in the total three-dimensional space.

In addition, if it may be assumed that 2$m$ additional sound sources 3 are arranged in a substantially uniform distribution on a spherical surface around the target sound source 1 which may be assumed a point sound source, the relationship of the expression (8) may be transformed to the following expression.

$$\frac{1}{m}\sum_{i=1}^{N}\{\cos k(x_p-d_i)+\cos k(x_p+d_i)\} - \cos k\cdot x_p \cong 0 \quad (9)$$

Therefore, the following relationship may be obtained.

$$\cos k\, d_i \cong 1 \quad (10)$$

The relationship means that the additional sound source 3 are preferably arranged as close as possible to the target sound source.

In addition, the measuring unit 5 may detect a rotating pulse signal of the engine 1 or an AC output signal produced by the generator 1$m$, as a signal relating to the sound from the target sound source, instead of the accelerating signal of the surface of the engine 1. If the measuring unit 5 detects the AC output signal produced by the generator 1$m$, since the signal may be produced by only a completely electric process, durability of the silencer may be improved than the case detecting the accelerating signal.

Second Embodiment

Figure 2:
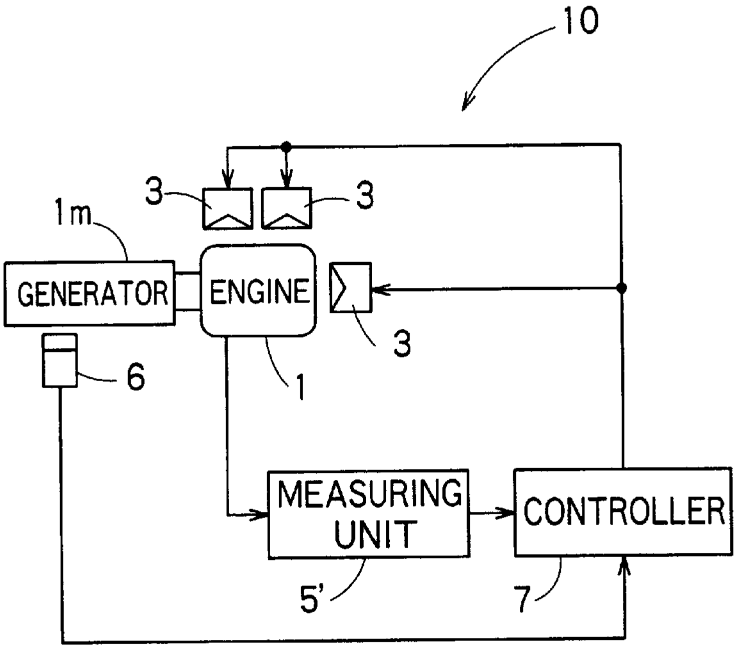
FIG. 2 is a schematic view of a second embodiment of a three-dimension active silencer according to the invention.

The second embodiment of the three-dimension active silencer is explained with reference to FIGS. 2 to 4. FIG. 2 is a schematic view of a second embodiment of the three-dimension active silencer according to the invention.

As shown in FIG. 2, the three-dimension active silencer of the second embodiment is provided for a small generator not contained in a closed box 4. N additional sound sources 3 are arranged in such a manner that a position $x_p$ of an engine 1 as a target sound source, respective relative positions $d_i$ (i=1, 2, . . . , N) of the N additional sound sources from the target sound source and a wave number k of the sound radiated from the target sound source can substantially satisfy a following relationship.

$$k|d_i| \leqq \pi/2 \quad (11)$$

A measuring unit 5' is adapted to detect an AC output signal produced by the generator 1$m$ and to make a sound-reference signal.

Other structures and components are substantially the same as the first embodiment shown in FIG. 1. The same reference numerals are used in the second embodiment for the same elements as in the first embodiment. The explanations of the same elements as the first embodiment are omitted.

Figure 3:
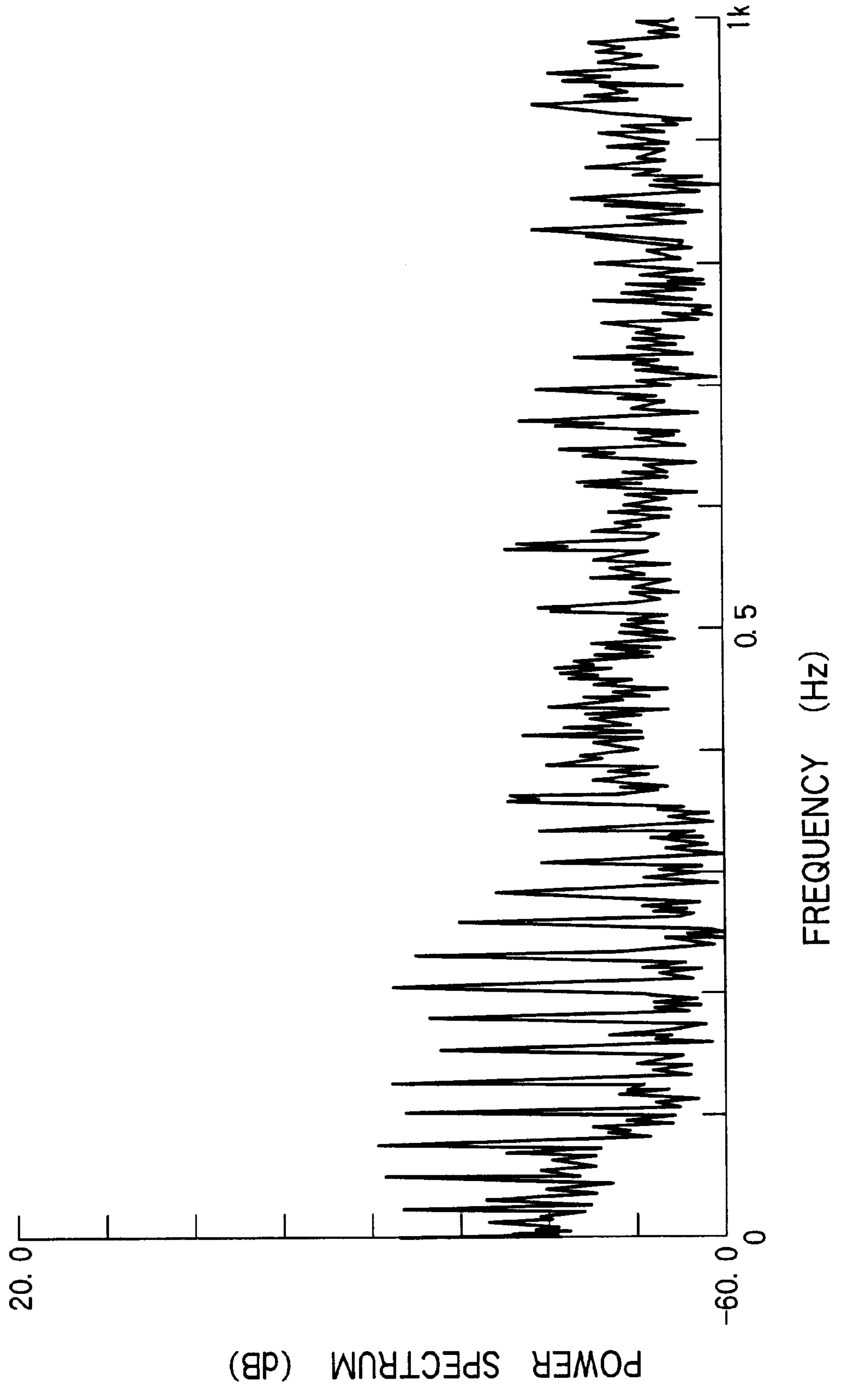
FIG. 3 is a graph showing a power spectrum of a sound radiated from a small generator shown in FIG. 2.

As shown in FIG. 3, an engine sound radiated from the small generator shown in FIG. 2 has eleven peaks that start from 25 Hz at intervals of 25 Hz.

Then, an operation of the second embodiment is explained below.

When the engine 1 is driven, the signal relating to the engine sound is detected by the measuring unit 5' and is inputted into the controller 7. The controller 7 adjusts the respective amplitudes and the respective phases of the additional sound sources 3, based on the signal detected by the measuring unit 5', in such a manner that the sound level detected by the microphone 6 is reduced to a minimum.

The measuring unit 5' detects an AC output signal produced by the generator 1*m*. An example of the detected signal is shown in FIG. 4. FIG. 4 shows a spectrum of a signal transformed to 2V by a transformer (not shown), from the AC output signal 100 V produced by the generator 1*m*.

Figure 4:
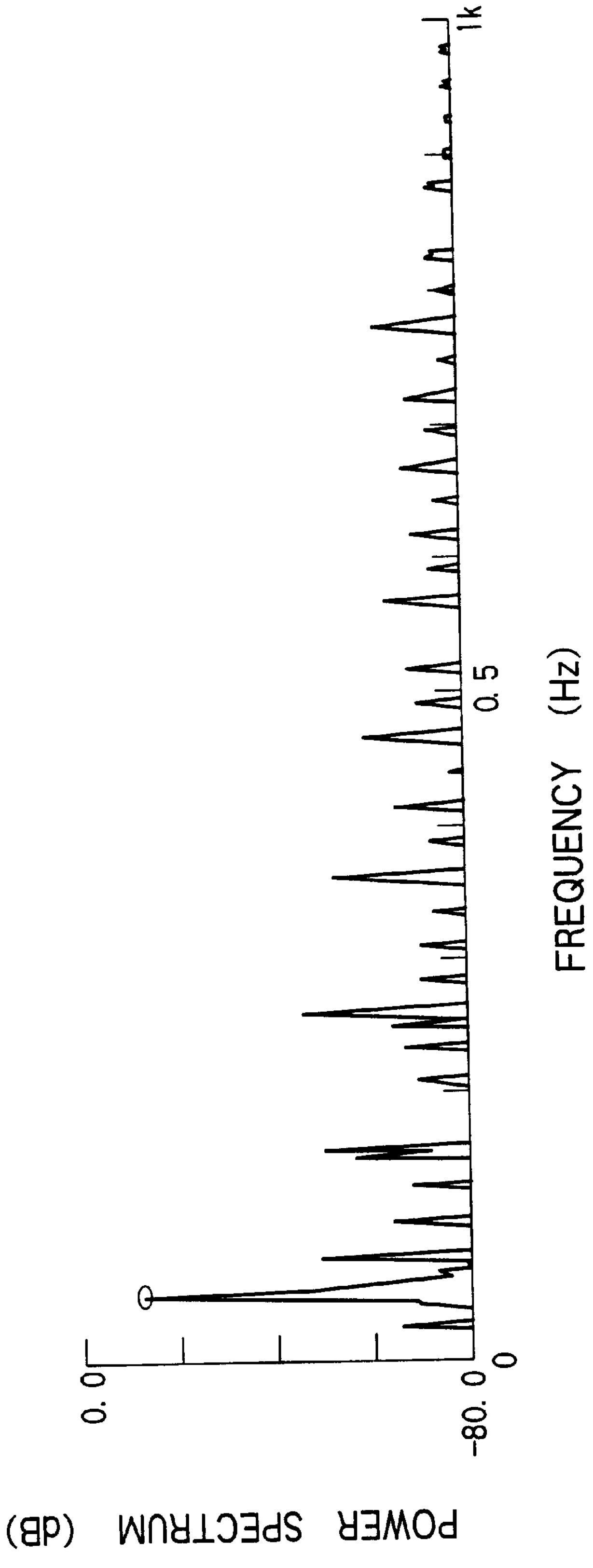
FIG. 4 is a graph showing a spectrum of an output signal from a small generator shown in FIG. 2.

As shown in FIG. 4, with regard to the AC output signal detected by the measuring unit 5', a peak of a basic frequency 25 Hz may be distinguished easily, but other peaks (see FIG. 3) may not be distinguished easily. Thus, it is not preferable to directly use the signal shown in FIG. 4 for the control by the controller 7.

Figure 5:
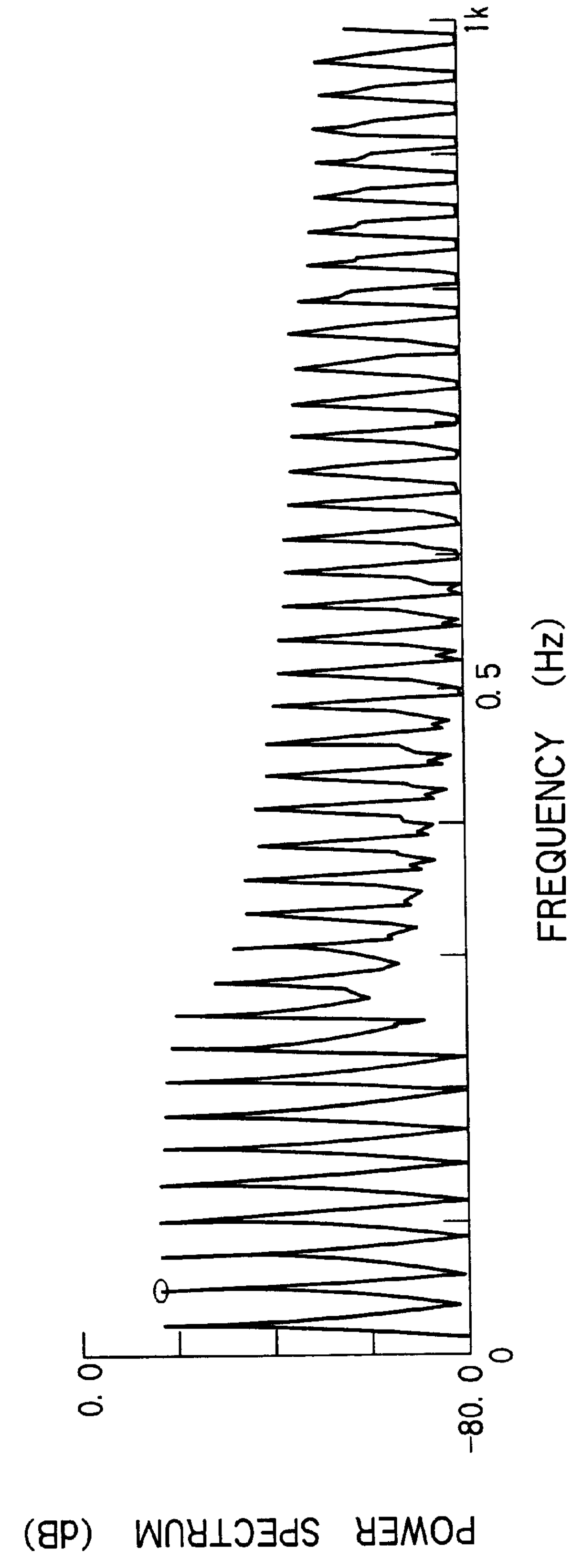
FIG. 5 is a graph showing an electric signal having peaks that are multiples of a basic frequency.
Figure 6:
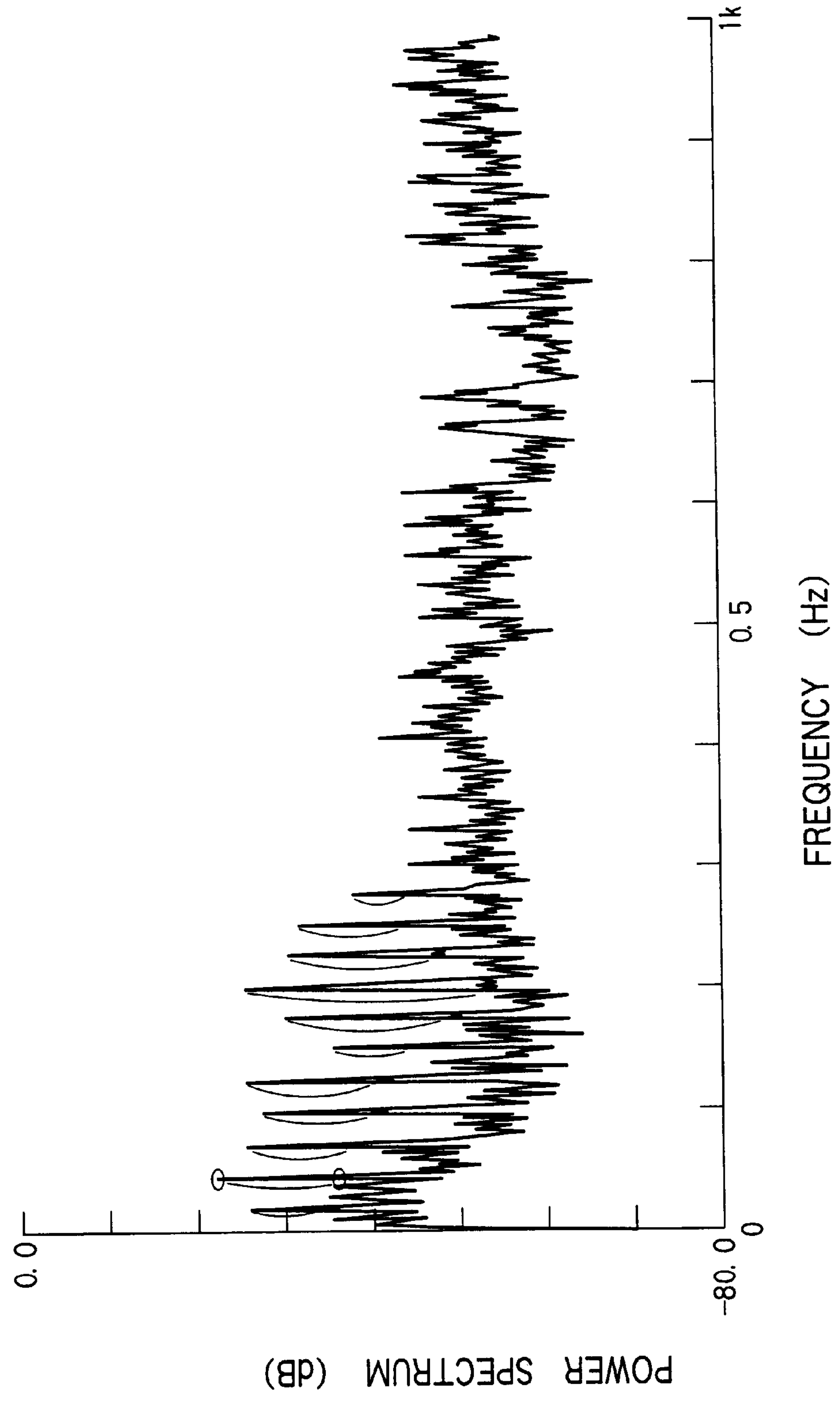
FIG. 6 is a graph showing an effect of the three-dimension active silencer shown in FIG. 2.

Therefore, the measuring unit 5' of the second embodiment artificially makes an electric signal shown in FIG. 5, which has peaks that are multiples of a basic frequency 25 Hz. Then, the measuring unit 5' synchronizes (with respect to phases) and overlaps the electric signal with the signal shown in FIG. 4 to produce a sound-reference signal. The sound-reference signal resembles the actual sound signal shown in FIG. 3 very much and is suitable for using for the control by the controllers 7. As a result, as shown in FIG. 6, all of the eleven peaks starting 25 Hz at the intervals of 25 Hz are reduced very well. The above process about the signal is a completely electric process, so that it needs less cost and less consideration for the durability of the silencer.

According to the above control by the controller 7, the sound power at the position where the microphone 6 is arranged can be reduced. However, the above control may not always achieve that a total acoustic power around the small generator is reduced to a minimum. In order to reduce the total acoustic power to the minimum, it is important where the additional sound sources 3 and the microphone 6 are arranged.

In the embodiment, the additional sound sources 3 are arranged with a special condition in order to reduce the total acoustic power around the small generator to the minimum. The special condition about an arrangement of the additional sound sources 3 is explained below.

At first, in the embodiment, the sound power is locally high at a cylinder section (a substantially center portion) in the engine 1. Thus, the target sound is radiated from the cylinder section in the same phase. That is, it is allowed to assume that the target sound source is a point sound source. Therefore, the engine sound can be treated by using a sound model that has a point sound source arranged in an open space.

It is assumed that one target sound source 1 and N additional sound sources 3 are arranged in an open space (all sound sources are point sound sources), the N additional sound sources 3 are arranged on a spherical surface around the target sound source 1, and the N additional sound sources have a common amplitude and a common phase. In the case, a ratio r of sound levels of a case wherein the N additional sound sources operate to another case wherein no additional sound sources operate is represented by the following expression.

$$r = \frac{W}{W_1} = 1 + \left(\frac{q_s}{q_p}\right)^2 \sum_{i=1}^{N} \sum_{j=1}^{N} \mathrm{sinc}(kd_{si-sj}) + 2N \cdot \left(\frac{q_s}{q_p}\right) \mathrm{sinc}(kd_{p-si}) \cos(\theta_S - \theta_p) \left(sic(x) = \frac{\sin x}{x}\right) \tag{12}$$

In the above expression (12), $\theta_p$ represents a phase of the target sound source, $q_p$ an amplitude of the target sound source, $\theta_s$ phases of the additional sound sources, and $q_s$ amplitudes of the additional sound sources, $d_{si-sj}$ a distance between two (i-th (i-listed) and j-th (j-listed)) additional sound sources; $d_{p-sj}$ a distance between the target sound source and a j-th (j-listed) additional sound sources (i, j=1, 2, . . . , N).

As seen in the expression (12), the total acoustic power changes dependently on the position, the phase $\theta_s$ and the amplitude $q_s$ of the additional sound sources 3.

A microphone 6 is arranged in the open space. Then, the controller 7 conducts an adaptation control (Filtered-X) to reduce a sound level detected by the microphone 6 to a minimum. The controlled situation is expressed by the following expression.

$$P(x_m) = [Z_p, Z_{s1}, \ldots, Z_{SN}][q_p, q_{s1}, \ldots, q_{SN}]_T = 0 \tag{2}$$

In the above expression (2), P represents a sound level and $x_m$ a position of the microphone. In addition, Z represent terms (functions) representing transmissions from the target sound source and the additional sound sources to the microphone, respectively. In addition, q represents a sound intensity (amplitude). Respective additional characters p and is represent the target sound source 1 and an i-th (i-listed) additional sound source 3.

Then, it is assumed that the N additional sound sources 3 generate additional sounds by means of a common controlling system. At that time, a ratio of the sound intensities between the target sound source 1 and the additional sound sources 3 ($q_s/q_p$) is expressed by the following expression.

$$\frac{q_s}{q_p} = -\frac{Z_p}{Z_s} = -\frac{\frac{\sin(kh_p)}{kh_p} + j\frac{\cos(kh_p)}{kh_p}}{\sum_{i=1}^{N}\left\{\frac{\sin(kh_{si})}{kh_{si}} + j\frac{\cos(kh_{si})}{kh_{si}}\right\}} \tag{13}$$

In the above expression (13), $h_p$ represents a distance between the target sound source 1 and the microphone 6, and $h_{si}$ represents a distance between the i-th (i-listed) additional sound 3 and the microphone 6. When the above relationship is substituted into the above expression (1), the total acoustic power under the adaptation control can be obtained.

Herein, if the additional sound sources 3 have a common amplitude and a common phase reverse to the target sound source, that is, if the N additional sound sources 3 satisfies the following expression (The amplitude is 1/N and the phase is reverse. The $e^{j\pi}$ means -1.), it is known that the total acoustic power can be considerably reduced if a frequency of the sound is not more than 200 Hz.

$$\frac{q_s}{q_p} = \frac{1}{N} e^{j\pi} \quad (5)$$

Thus, a relationship of hp $h_p \approx h_{si}$ can be obtained from a condition of the amplitude ratio 1/N in the expression (5).

Figure 7A:
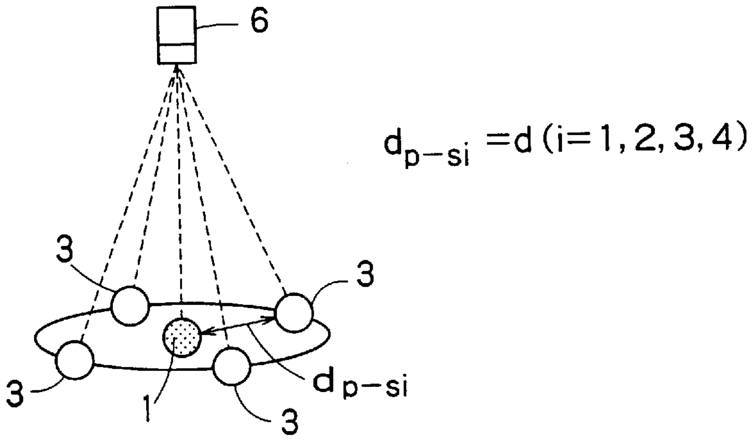
FIGS. 7A and 7B are schematic views showing preferable examples of arrangements of additional sound sources in the three-dimension active silencer shown in FIG. 2.
Figure 7B:
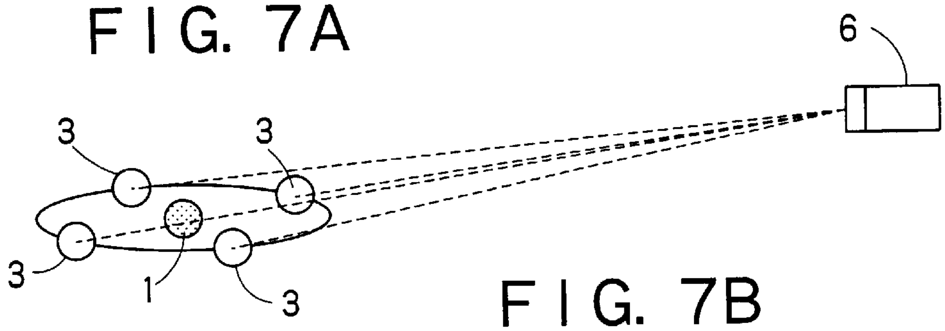
Figure 8:
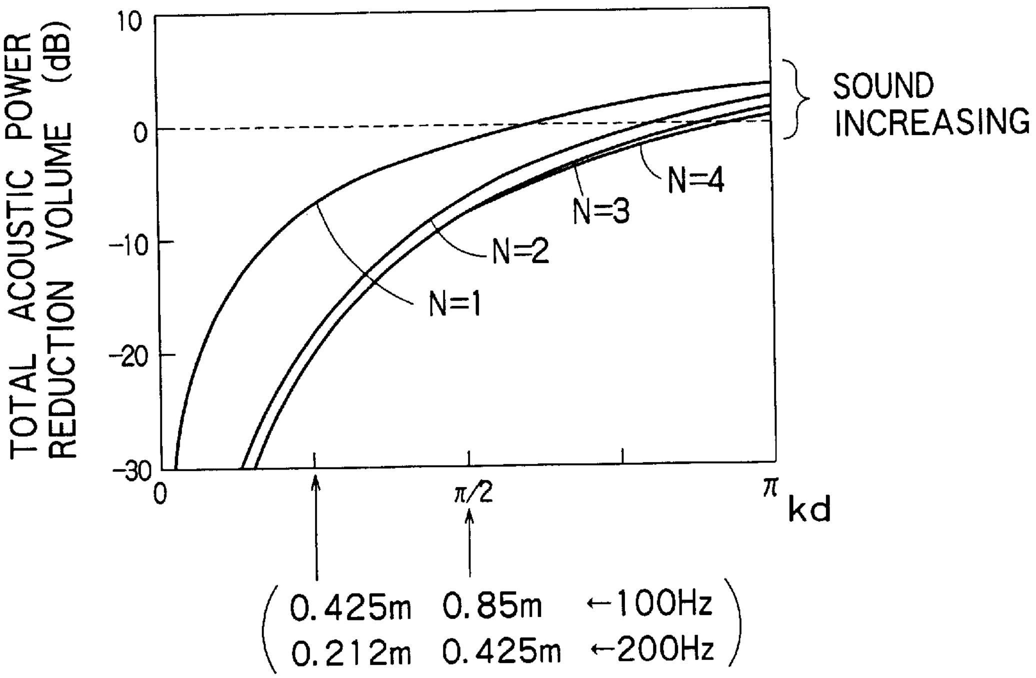
FIG. 8 is a graph showing a reduction effect of the total acoustic power in the three-dimension active silencer shown in FIG. 2.

FIGS. 7A and 7B show two examples of arrangements of the additional sound sources 3 and the microphone 6 that satisfy the relationship of $h_p \approx h_{si}$. FIG. 8 shows relationship between a parameter kd and a reduced total acoustic power, in the case of the arrangement shown in FIG. 7A ($d_{p-si}$=d), wherein the number of the additional sound sources is 1 to 4. From a result shown in FIG. 8, it is confirmed that the total acoustic power may be considerably reduced if $kd_{p-si}$ (=k $|d_i|$)π/2(i=1, 2, . . . , N).

Figure 9A:
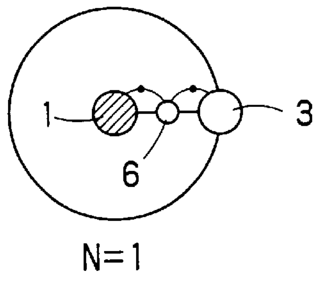
FIGS. 9A to 9D are schematic views showing other preferable examples of arrangements of additional sound sources in the three-dimension active silencer shown in FIG. 2.
Figure 9C:
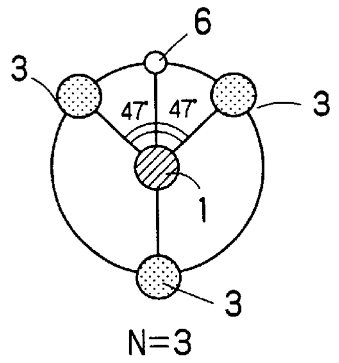
Figure 9B:
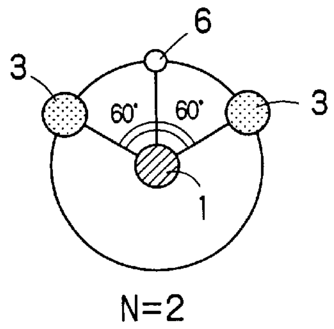
Figure 9D:
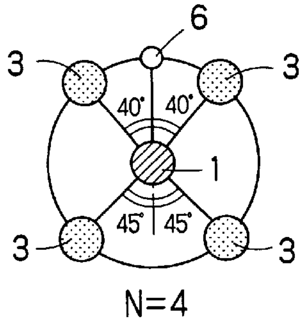

In addition, it is found that arrangements shown in FIGS. 9A and 9D are much suitable if the additional sound sources 3, the microphone 6 and the target sound source 1 are arranged in a plane.

As described above, if the N additional sound sources 3 are arranged in such a manner that the expression (11) is satisfied, the total acoustic power around the small generator can be reduced to a minimum. That is, according to the embodiment, the total acoustic power can be reduced to the minimum in the total three-dimensional space.

Third Embodiment

Figure 10:
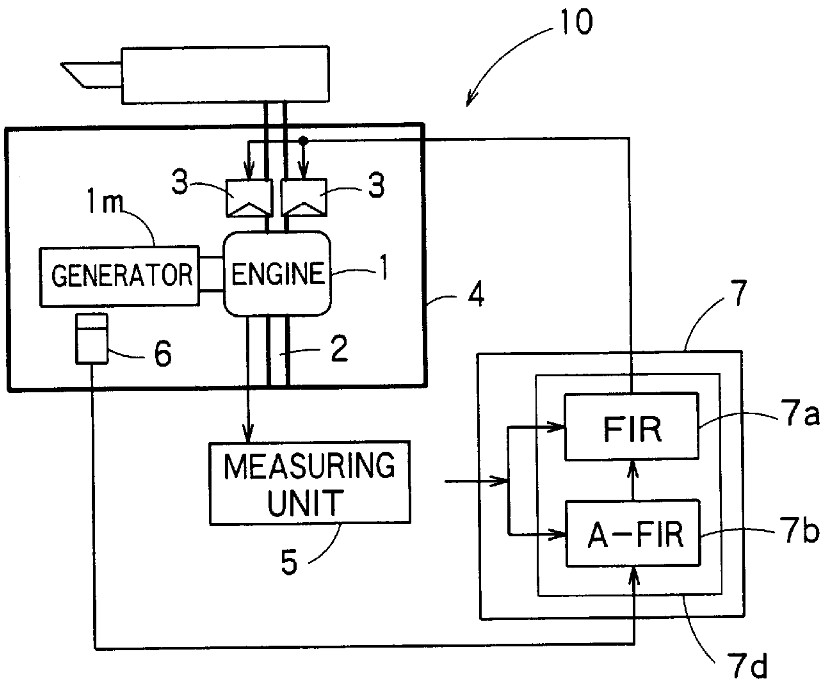
FIG. 10 is a schematic view of a third embodiment of a three-dimension active silencer according to the invention.

The third embodiment of the three-dimension active silencer is explained with reference to FIG. 10. FIG. 10 is a schematic view of a third embodiment of the three-dimension active silencer according to the invention.

As shown in FIG. 10, in the three-dimension active silencer of the third embodiment, a controller 7 has a digital controlling part 7*d* including a controlling-coefficient calculator 7*a* which calculates controlling coefficients and a controlling-coefficient processor 7*b* which calculates a sum of products of the controlling coefficients and the signal. In addition, the controlling coefficients are adapted to be updated substantially every moment.

Other structures and components are substantially the same as the first embodiment shown in FIG. 1. The same reference numerals are used in the third embodiment for the same elements as in the first embodiment. The explanations of the same elements as the first embodiment are omitted.

According to the third embodiment, since the controlling coefficients are updated substantially every moment, the control can effectively follow a change caused by the passage of time, such as a temperature change of an inside and/or outside of the generator box 4, a pulsation of the engine 1 or a sound-level (sound-pressure) change caused by a load change. As a result, the sound level detected by the microphone 6 can be stably reduced to a minimum and the total acoustic power can be also stably reduced to a minimum.

The feature of the third embodiment can be also adopted in the three-dimension active silencer of the second embodiment.

Fourth Embodiment

Figure 11:
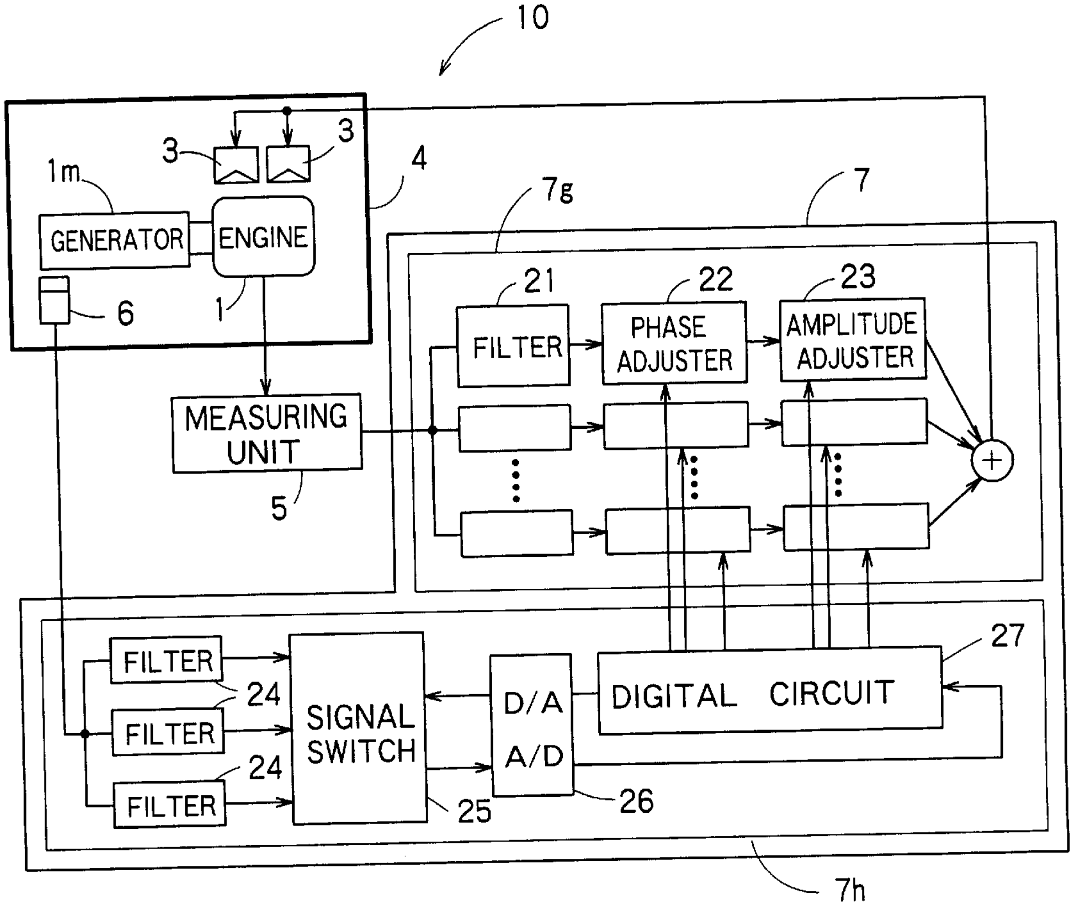
FIG. 11 is a schematic view of a fourth embodiment of a three-dimension active silencer according to the invention.

The fourth embodiment of the three-dimension active silencer is explained with reference to FIG. 11. FIG. 11 is a schematic view of a fourth embodiment of the three-dimension active silencer according to the invention.

As shown in FIG. 11, in the three-dimension active silencer of the fourth embodiment, a controller 7 has: an analogue controlling part 7*g* including first band-pass filters 21, phase adjusters 22 and amplitude adjusters 23; and an acoustic-power (sound-pressure) monitoring part 7*h* including second band-pass filters 24, a signal switch 25, an AD/DA converter 26 and a digital circuit 27.

Other structures and components are substantially the same as the first embodiment shown in FIG. 1. The same reference numerals are used in the fourth embodiment for the same elements as in the first embodiment. The explanations of the same elements as the first embodiment are omitted.

The controller 7 of the fourth embodiment conducts a filtering process to an output signal from the measuring unit 5 by means of the first band-pass filters 21. Then, the controller 7 advances a phase of the signal by a degree from 0 to 180 or delays the phase by a degree from 0 to 180.

In addition, the controller 7 always monitors an acoustic-power (sound-pressure) signal detected by the microphone 6. The controller 7 conducts a filtering process to the sound-level signal by means of the second band-pass filters 24. The filtered signal is transmitted to the digital circuit 27 via the signal switch 25 and the AD/DA converter 26.

The digital circuit 27 transmits an instructing signal to each of the phase adjusters 22 so that the phase is adjusted to lead the monitored sound level (detected by the microphone) to a minimum. Once it is confirmed that the monitored sounds level is led to the minimum, the phase is fixed. Then, each of the amplitude adjusters 23 conducts an amplitude-level adjusting process in order to reduce the microphone sound level further. The digital circuit 27 transmits an instructing signal to each of the amplitude adjusters 23 so that the phase is adjusted to lead the monitored sound level (detected by the microphone) to a further minimum.

The controller 7 repeats the above adjustment for every target frequency. Then, finally, the controller 7 generates a sound having an optimum phase and an optimum amplitudes and outputs it from the additional sound sources 3.

According to the fourth embodiment, since the controller 7 has the analogue controlling part 7*g* and the acoustic-power (sound-pressure) monitoring part 7*h* to automatically adjust the phase and the amplitude for the additional sound sources 3 to their optima, the control can effectively follow a change caused by the passage of time, such as a temperature change of an inside and/or outside of the generator box 4, a pulsation of the engine 1 or a sound-level (sound-pressure) change caused by a load change. As a result, the sound level detected by the microphone 6 can be stably reduced to a minimum and the total acoustic power can be also stably reduced to a minimum.

The feature of the fourth embodiment can be also adopted in the three-dimension active silencer of the second embodiment.

Fifth Embodiment

Figure 12:
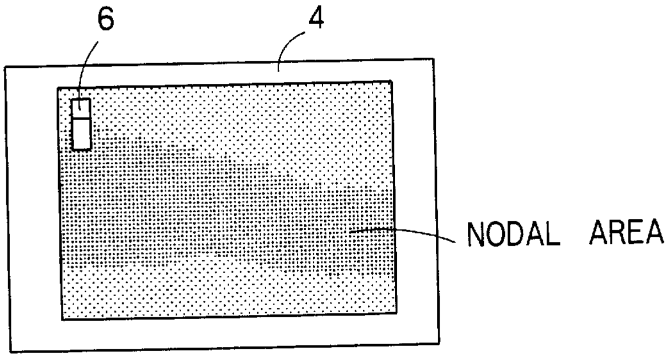
FIG. 12 is a view showing an area where a microphone is preferably arranged, in a fifth embodiment of a three-dimension active silencer according to the invention.

The fifth embodiment of the three-dimension active silencer is explained with reference to FIG. 12. FIG. 12 is a schematic view of a fifth embodiment of the three-dimension active silencer according to the invention.

As shown in FIG. 12, in the three-dimension active silencer of the fifth embodiment, a microphone 6 is arranged in an area which is not in a node area of the sound radiated from an engine 1 as a target sound source in a closed box and which is not in node areas of additional sounds radiated from the additional sound sources 3 in the closed box.

Other structures and components are substantially the same as the first embodiment shown in FIG. 1. The same reference numerals are used in the fifth embodiment for the same elements as in the first embodiment. The explanations of the same elements as the first embodiment are omitted.

In the fifth embodiment, the microphone 6 is arranged with a special condition. The special condition is led from a fact that: when the microphone 6 is arranged in the nodal area (minimum-sound-pressure area) made by only the additional sound sources 3, a denominator of the above expression (4) becomes zero and the control undesirably diverges; and a fact that: when the microphone 6 is arranged in the nodal area (minimum-sound-pressure area) made by only the target sound source 1, a numerator of the above expression (4) becomes zero and the control is not conducted.

In the fifth embodiment, the phase $\theta_{si}$ and the amplitude $q_{si}$ of the additional sound sources 3 that can achieve to reduce the total acoustic power W defined by the expression (1) to a minimum, must satisfy the following expression in theory.

$$\frac{dW}{d\theta_{si}} = 0, \frac{dW}{dq_{si}} = 0 \tag{14}$$

Thus, $q_{si}/q_p$ can be obtained from the expression (14). If the qsi/sp is substituted into the expression (1), a minimum total acoustic power can be obtained. A minimum solution of the total acoustic power in theory is shown in FIG. 13.

Figure 13:
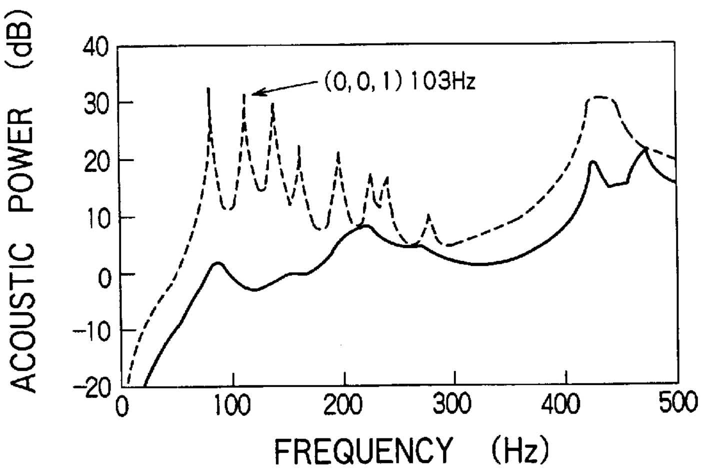
FIG. 13 is a graph showing a theoretical minimum of the total acoustic power.

Values shown in FIG. 13 are minima in theory. Thus, the adaptation control by the controller 7 can achieve the minimum acoustic powers for not every frequency. However, the adaptation control can make a minimum acoustic power for a special target frequency get closer to a theoretical value shown in FIG. 13.

Figure 14:
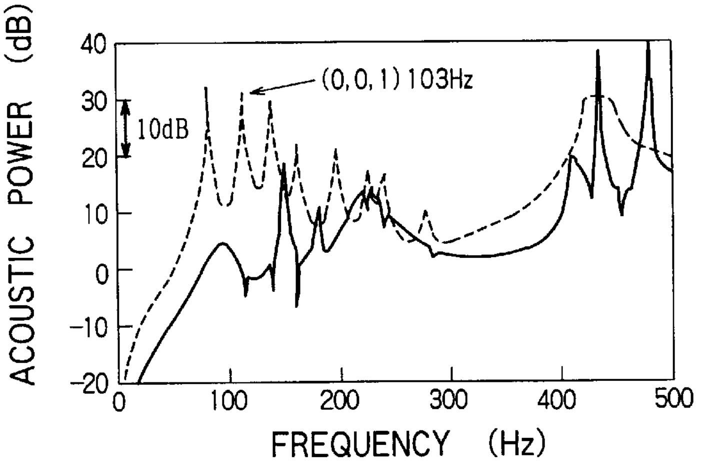
FIG. 14 is a graph showing a reduction effect of the total acoustic power when the target sound source radiates a sound having a frequency of 103 Hz.

For example, a sound in the embodiment has a peak frequency of 103 Hz. Thus, if the frequency of 103 Hz is set as a special target frequency, an overall acoustic power can be reduced effectively. FIG. 14 shows a graph of a relationship between the frequencies and the total acoustic powers when the control is conducted for a special target frequency of 103 Hz.

As described above, according to the fifth embodiment, an acoustic power W for a predetermined target frequency can be gotten closer to a theoretical minimum value.

In addition, a calculation of the acoustic power W is conducted for each of many positions where the microphone 6 is arranged under the above condition. It is found from the calculation that the acoustic power W can be effectively reduced to a minimum when the microphone 6 is arranged at a corner portion of the closed box 4, especially when the microphone 6 is arranged in such a manner that a distance d from the corner and a wavelength α of the sound satisfy the following expression.

$$d \leqq \frac{\lambda}{2\pi} \tag{15}$$

Herein, in the above embodiments, the target sound source is treated as the point sound source located in the center of the engine 1 because it is assumed that the sound radiated from the engine 1 is much larger than the sound radiated from the exhaust duct 2. If the sound from the exhaust duct 2 is so large that it should not be ignored, an optimum arrangement question should be solved with another model having such an additional target sound source.

Sixth Embodiment

The sixth embodiment of the three-dimension active silencer is explained with reference to FIG. 15.

In the three-dimension active silencer of the sixth embodiment, the additional sound sources 3 are arranged in such manner that the following expression is satisfied as described ith regard to the second embodiment.

$$k|d_i| \leqq \pi/2 \tag{11}$$

Especially, in the case, the additional sound sources 3 are arranged in such a manner that the following expression is satisfied.

$$|d_{i\;|=d=\lambda/}4(k|d_i|=\pi/2) \tag{16}$$

Figure 15:
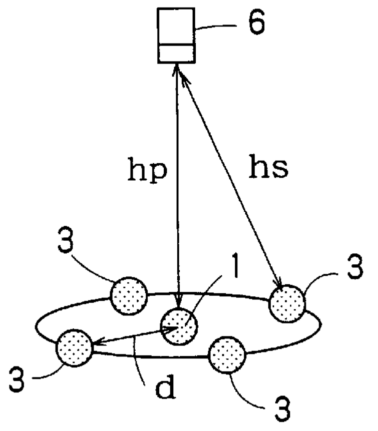
FIG. 15 is a schematic view showing a preferable arrangement of a target sound source, additional sound sources and a microphone, in a sixth embodiment of the three-dimension active silencer.

In addition, as shown in FIG. 15, the target sound source 1 and the additional sound sources 3 are arranged in substantially the same plane, and the microphone 6 is arranged on a perpendicular line extending from the target sound source 1 perpendicular to the above plane.

As shown in FIG. 15, when hp and hs represent a distance between the microphone 6 and the target sound source 1 and a distance between the microphone 6 and each of the additional sound sources 3, respectively, a phase difference θ of the additional sound sources 3 relative to the target sound source 1 is expressed by the following expression.

$$\theta = 2\pi f\ (h\ s - h\ p)/C + \pi$$

$$(h\ s = \sqrt{}h\ p^2 + d^2) \tag{17}$$

In the sixth embodiment, as seen in the expression, (17), if hp=d=λ/4, the phase is shifted by 37 degrees from 180 degrees which is a condition of the minimum acoustic power. In addition, if hp=d/2=λ/8, the phase is shifted by 55 degrees. However, in a frequency area less than 200 Hz, the acoustic-power can be reduced although the degree of the acoustic-power reduction is lowered. Therefore, if the microphone 6 is arranged within λ /4 from the target sound source 1 similarly to the additional sound sources 3, the acoustic power can be reduced effectively.

Figure 16A:
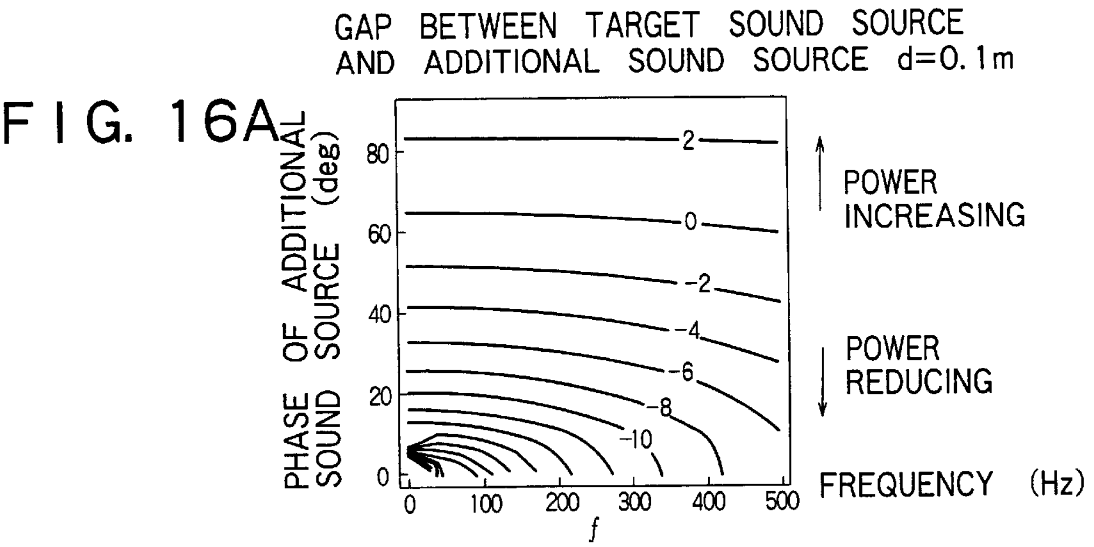
FIGS. 16A to 16C are graphs showing reduction effects of the total acoustic power in the three-dimension active silencer shown in FIG. 15.
Figure 16B:
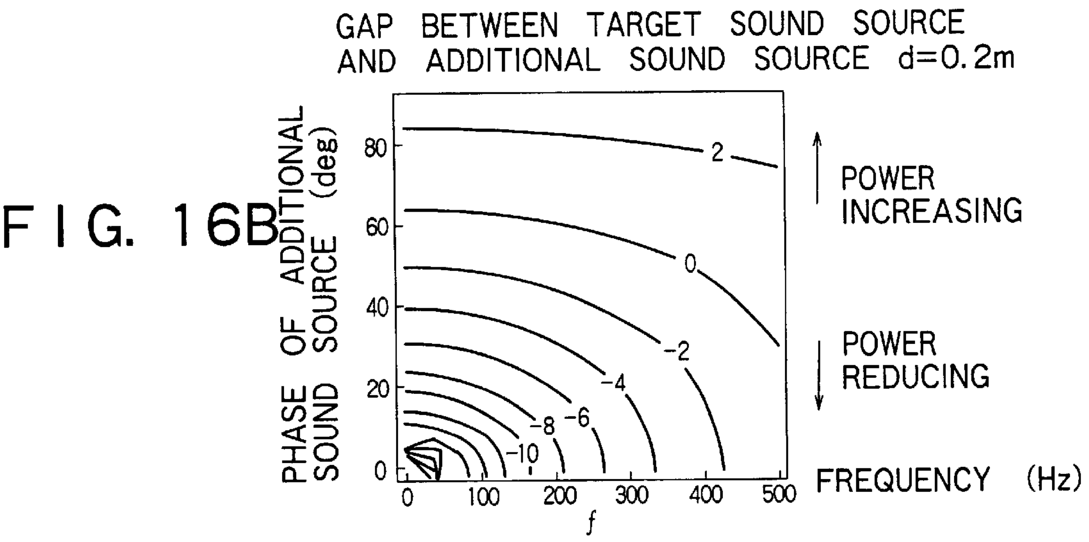
Figure 16C:
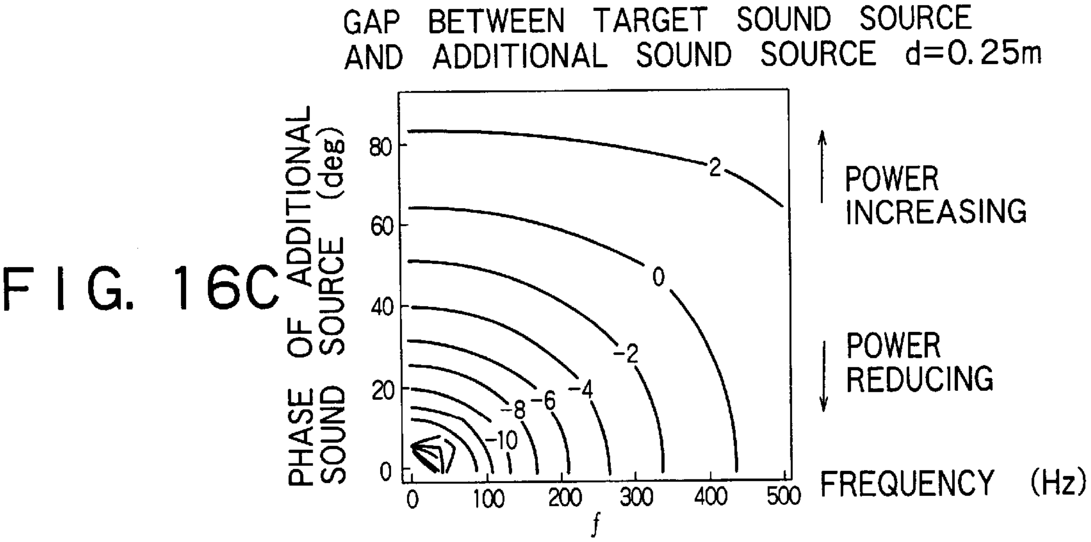

FIGS. 16A to 16C show results of actual experiments. As seen from the results shown in FIGS. 16A to 16C, enough effects of the acoustic-power reduction can be obtained in cases of d=0.10 m, d=0.20 m and d=0.25 m, respectively. Herein, a frequency of 200 Hz corresponds to λ=1.7 m, that is, λ/4=0.425 m.

Seventh Embodiment

The seventh embodiment of the three-dimension active silencer is explained with reference to FIG. 17. The three-dimension active silencer of the seventh embodiment 30 is intended to reduce acoustic powers (sound pressures) radiated from a first target sound source 31 and a second target sound source 32.

Figure 17:
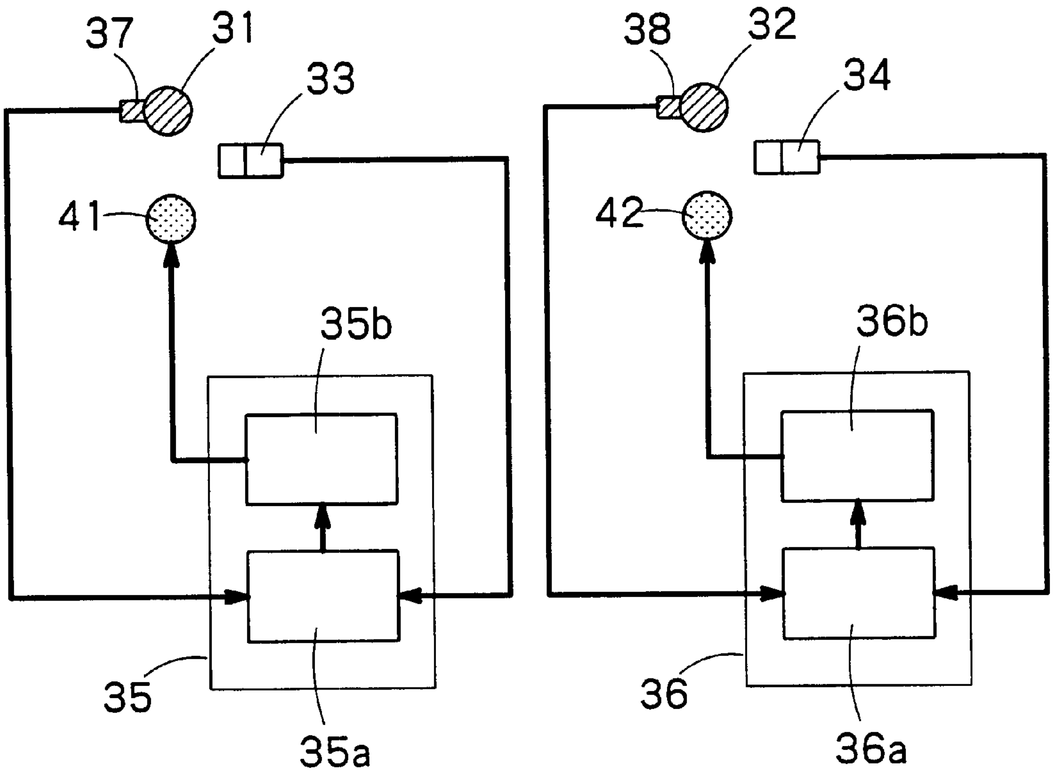
FIG. 17 is a schematic view of a seventh embodiment of a three-dimension active silencer according to the invention.

As shown in FIG. 17, a first additional sound source 41 is arranged around the first target sound source 31. In addition, a first microphone 33 is arranged at a predetermined position, for example close to the first target sound source 31. In addition, a sensor 37 such as an acceleration sensor is provided around the first target sound source 31, for detecting a signal relating to a sound radiated from the first target sound source 31 and for transmitting the signal to a first controller (first controlling circuit) 35 as an inputting signal.

The first controller 35 has a controlling-coefficient calculator 35*a* which calculates adaptive controlling coefficients substantially every moment and a controlling-coefficient processor 35*b* which calculates a sum of products of the controlling coefficients with the inputting signal land outputs the sum. In addition, the first controller 35 is adapted to control a phase and an amplitude of the first additional sound source 41 by using the sum outputted from the controlling-coefficient processor 35*b* in such a manner the sound level detected by the first microphone 33 is reduced to a minimum.

The first additional sound source 41 has a speaker, and is adapted to receive the sum outputted from the controlling-coefficient processor 35*b* as an inputted signal to supply an energy for silencing the target sound.

The first microphone 33 is adapted to detect a sum of the sounds from the first target sound source 31 and the first additional sound source 41, and to function as an error-signal detector that regards the sum as an error signal.

Similarly, a second additional sound source 42 is arranged around the second target sound source 32. In addition, a second microphone 34 is arranged at a predetermined position, for example close to the second target sound source 32. In addition, a sensor 38 such as an acceleration sensor is provided around the second target sound source 32, for detecting a signal relating to a sound radiated from the second target sound source 32 and for transmitting the signal to a second controller (first controlling circuit) 36 as an inputting signal.

The second controller 36 has a controlling-coefficient calculator 36*a* which calculates adaptive controlling coefficients substantially every moment and a controlling-coefficient processor 36*b* which calculates a sum of products of the controlling coefficients with the inputting signal and outputs the sum. In addition, the second controller 36 is adapted to control a phase and an amplitude of the second additional sound source 42 by using the sum outputted from the controlling-coefficient processor 36*b* in such a manner the sound level detected by the second microphone 34 is reduced to a minimum.

The second additional sound source 42 has a speaker, and is adapted to receive the sum outputted from the controlling-coefficient processor 36*b* as an inputted signal to supply an energy for silencing the target sound.

The second microphone 34 is adapted to detect a sum of the sounds from the second target sound source 32 and the second additional sound source 42, and to function as an error-signal detector that regards the sum as an error signal.

Figure 18:
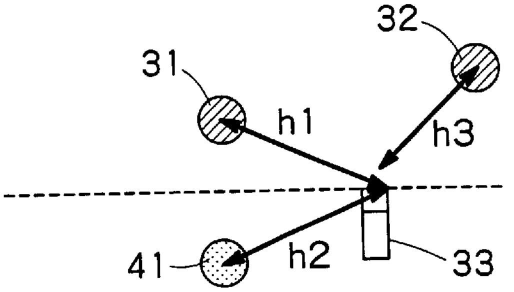
FIG. 18 is a schematic view showing an arrangement of two target sound sources, a first additional sound source and a microphone, in the seventh embodiment of the three-dimension active silencer.

Then, a model ignoring an effect of the second additional sound source 42 is assumed. As shown in FIG. 18, when $h_1$ represents a distance between the first target sound source 31 and the first microphone 33, $h_2$ a distance between the first additional sound source 41 and the first microphone 33, $h_3$ a distance between the second target sound source 32 and the first microphone 33, $A_1$ an amplitude of the first target sound source 31, $A_2$ an amplitude of the first additional sound source 41, $\theta$ a phase of the first additional sound source 41 with respect to the first target sound source 31, and $A_3$ an amplitude of the second target sound source 32, the acoustic power (sound pressure) detected by the first microphone 33 is expressed by the following expression (18).

$$P = \frac{A_1}{h_i}e^{-jkh_1} + \frac{A_2}{h_2}e^{-j(kh_2+\theta)} + \frac{A_3}{h_3}e^{-jkh_3} \tag{18}$$

Thus, an optimum amplitude and an optimum phase of the first additional sound source 41, which can be obtained under the condition wherein the sound level detected by the first microphone 33 is reduced to a minimum by the adaptation control, satisfy the following expression (20) under the following expression (19).

$$|P|^2 = \left(\frac{A_1}{h_1}\right)^2 + \left(\frac{A_2}{h_2}\right)^2 + \left(\frac{A_3}{h_3}\right)^2 + \frac{2A_1A_2}{h_1h_2}\cos[k(h_1-h_2)-\theta] + \frac{2A_1A_3}{h_1h_3}\cos[k(h_1-h_3)] + \frac{2A_2A_3}{h_2h_3}\cos[k(h_2-h_3)+\theta] \tag{19}$$

$$\frac{\partial|P|^2}{\partial A_2} = 0,\ \frac{\partial|P|^2}{\partial\theta} = 0 \tag{20}$$

That is, the optimum amplitude and the optimum phase of the first additional sound source 41 satisfy the following expressions (21) and (22).

$$\theta = \tan^{-1}\frac{\frac{\alpha}{h_3}\sin[k(h_2-h_3)]}{\frac{1}{h_1} - \frac{\alpha}{h_3}\cos[k(h_2-h_3)]} \tag{21}$$

$$\frac{A_2}{A_1} = -\frac{\frac{1}{h_1h_2}\cos[k(h_1-h_2)-\theta] + \frac{\alpha}{h_2h_3}\cos[k(h_2-h_3)-\theta]}{\left(\frac{1}{h_2}\right)^2} \tag{22}$$

Herein, as expressed in the following expression (23), $\alpha$ is a ratio of the amplitude $A_2$ of the second target sound source 32 relative to the amplitude $A_1$ of the first target sound source 31.

$$\alpha = \frac{A_3}{A_1} \tag{23}$$

If the ratio $\alpha=0$ (the second target sound source 32 is not driven), $h_1=h_2$ satisfy the following expression (24). That is, $h_1=h_2$ is an optimum condition that can reduce the acoustic power of the first target sound source 31 to a minimum.

$$\theta \to \pi,\ \frac{A_2}{A_1} \to 1 \tag{24}$$

However, actually, the ratio $\alpha$ is not 0. Thus, because of the effect of the second target sound source 32, the amplitude and the phase of the first additional sound source 41 may be shifted from their optima expressed by the above expression (24). If the amplitude ratio $\alpha$ is constant, the amplitude and the phase of the first additional sound source 41 can be compensated from the expressions (21) and (22) by taking the ratio $\alpha$ into consideration. However, if the amplitude ratio $\alpha$ changes during the passage of time, it is difficult to conduct such a compensation.

Therefore, at first, it is intended to silence the sound power from the second target sound source 32.

Figure 19:
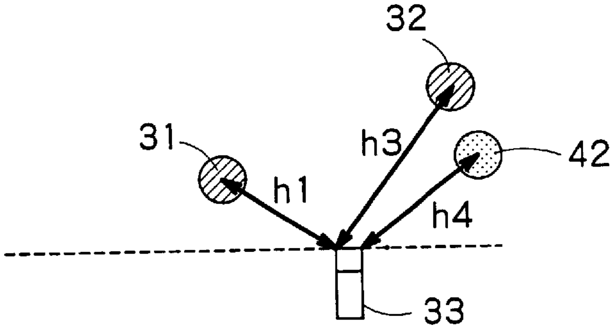
FIG. 19 is a schematic view showing an arrangement of the two target sound sources, a second additional sound source and the microphone, in the seventh embodiment of the three-dimension active silencer.

As shown in FIG. 19, h4 represents a distance between the second additional sound source 42 and the first microphone 33. If the second additional sound source 42 is arranged closer to the target sound source 32 in such a manner that the relationship $h_3=h_4$ is satisfied and the first microphone 33 is arranged in such a manner that the relationship $h_1<h_3$ is satisfied, the sound level detected by the first microphone 33 is expressed by the following expression (25).

$$P = \frac{A_1}{h_i}e^{-jkh_1} + \frac{A_3}{h_3}e^{-jkh_3} + \frac{A_4}{h_4}e^{-j(kh_4+\pi)}|P|^2 = A_1^2\left\{\left(\frac{1}{h_1}\right)^2 + \left(\frac{1}{h_3}\right)^2 + \left(\frac{1}{h^4}\right)^2 + \frac{2\alpha^2}{h_1h_3}\cos[k(h_1-h_3)] - \right. \tag{25}$$

-continued $$\left.\frac{2\alpha^2}{h_1 h_4}\cos[k(h_1 - h_4)] - \frac{2\alpha^2}{h_3 h_4}\cos[k(h_3 - h_4)]\right\} \text{ if } h_3 =$$

$$h_4.\ |P|^2 = A_1^2\left[\left(\frac{1}{h_1}\right)^2 + 2\left(\frac{\alpha}{h_3}\right)^2 - \frac{2\alpha^2}{(h_3)^2}\right] \rightarrow \left(\frac{A_1}{h_1}\right)^2$$

That is, in the case, the first microphone 33 can detect only the sound radiated from the first target sound source 3*l*.

In addition, an optimum condition for the second additional sound source 42 can be obtained by arranging the second microphone 34 at a position where a volume velocity of the second target sound source 32 is substantially equal to a volume velocity of the additional sound source 42. That is, the suitable position where the second microphone 34 should be arranged is in a minimum-acoustic-power area that is formed by the second additional sound source 42 having a same amplitude and a reverse phase with respect to the second target sound source 32. For example, it is assumed that one second additional sound source 42 is used against one second target sound source 32. In the case, the suitable position where the second microphone 34 should be arranged is located close to the second target sound source 32 and in such a manner that a distance between the suitable position and the second target sound source 32 is substantially equal to a distance between the suitable position and the second additional sound source 42. Preferably, the suitable position is substantially intermediate between the second target sound source 32 and the second additional sound source 42. If the second microphone 34 is arranged in such a manner, the second microphone 34 detects the sound radiated from the second target sound source 32 relatively more than the sound radiated from the first target sound source 31, even if both of the target sound sources 31 and 32 are driven at the same time. Thus, the optimum condition for the second additional sound source 42 can be obtained when the sound level at the position where the second microphone 34 is arranged is reduced to a minimum by the adaptation control.

In addition, with regard to the number of the second additional sound source, a plurality of the second additional sound sources can be arranged around the second target sound source 32. In the case, it is preferable that a blowing volume velocity of the second target sound source 32 is substantially equal to a sum of absorption volume velocities of the plurality of the second additional sound sources.

The seventh embodiment is suitable when the sound radiated from the second target sound source 32 has a substantially same frequency, a delayed amplitude and a delayed phase, with respect to the sound radiated from the first target sound source 31'. For example, the second target sound source 32 may be a supplement machine, which is arranged close to the first target sound source 31 and to which the sound can be transmitted via one or more solid from the first target sound source 31. In the case, the second target sound source 32 is called a secondary sound source.

Then, an effect of the seventh embodiment is explained with results of experiments.

Figure 20:
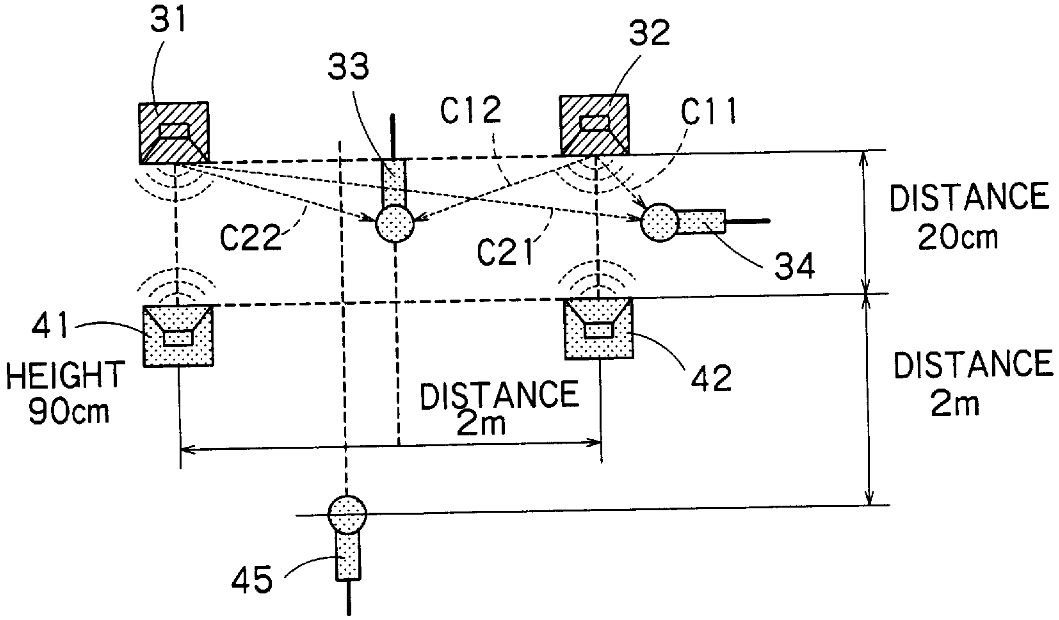
FIG. 20 is a schematic view showing an arrangement of the two target sound sources, the first and second additional sound sources and the microphones, used in actual experiments.
Figure 21:
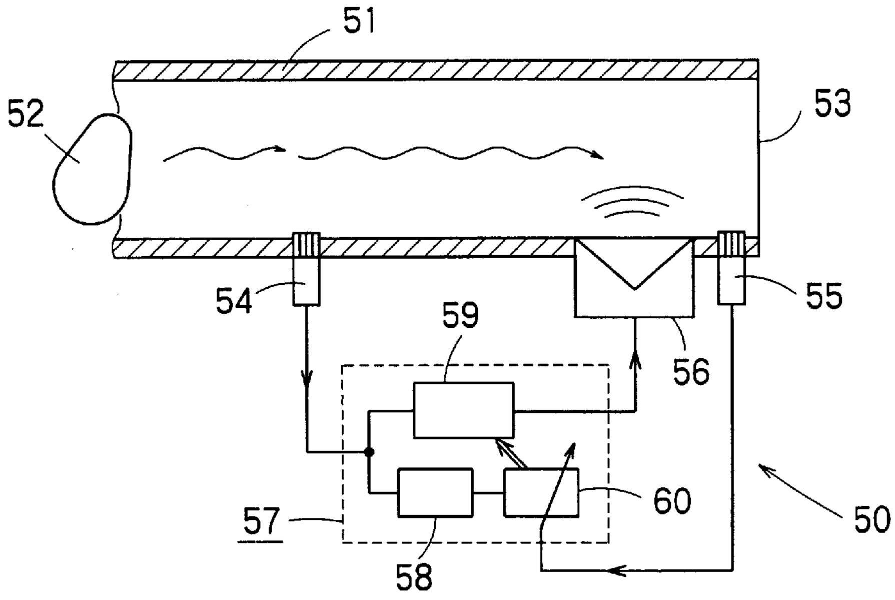
FIG. 21 is a schematic view of a conventional one-dimension active silencer.
Figure 22:
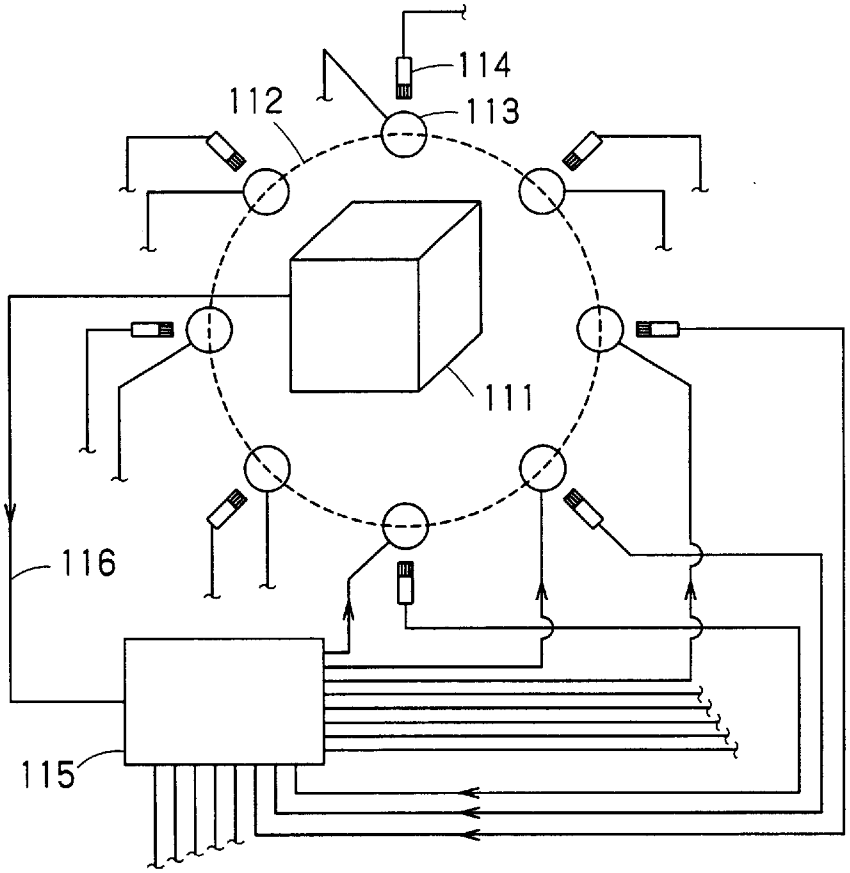
FIG. 22 is a schematic view of a conventional three-dimension active silencer.

In the experiments, as shown in FIG. 20, the first target sound source 31 consists of a speaker, and the second target sound source 32 consists of another speaker. In addition, the first additional sound source 41 is arranged to face the first target sound source 31, and the second additional sound source 42 is arranged to face the second target sound source 32.

The first microphone 33 is arranged at a position at the same distance from the first target sound source 31 and from the second target sound source 32 so that the first microphone 33 can also detect the sound radiated from the second target sound source 32. In addition, the position where the first microphone 33 is arranged is at the same distance from the first target sound source 31 and from the first additional sound source 41. That is, at the position, the acoustic power of the first target sound source 31 is minimum when the second target sound source is not driven.

On the other hand, the second microphone 34 is arranged close to the second target sound source so that the second microphone 34 is hard to detect the sound radiated from the first target sound source 31.

Under the above condition, a sound having a frequency of. 200 Hz was generated by both of the first target sound sources 31 and the second target sound source 32. Gains and phases of respective transmitting functions C11, C12, C21 and C22 from respective target sound sources 31 and 32 to respective microphones 33 and 34 were examined. The results are shown in Table 1.

TABLE 1

| Transmitting Function (200 Hz) | Gain (dBV) | Phase (deg) |
|---|---|---|
| C11 | 27.7 | 40 |
| C12 | 4.13 | −104.4 |
| C21 | 4.37 | −66.2 |
| C22 | 2.21 | −86 |

Next, Table 2 shows the effect of the case where only the first target sound source 31 was driven and only the first additional sound source 41 was used for the silencing control.

TABLE 2

| | First Microphone | Second Microphone | Third Microphone |
|---|---|---|---|
| Before Control | 75.0 | 75.0 | 78.7 |
| During Control | 48.3 | 47.7 | 69.4 |

As shown in Table 2, the sound level detected by the first microphone 33 was reduced from 75.0 dB to 48.3 dB. In addition, the sound level detected by the second microphone 34 was reduced from 75.0 dB to 47.7 dB. Furthermore, the sound level detected by the third microphone 150 arranged at a position shown in FIG. 20 was reduced from 78.7 dB to 69.4 dB. The experimenter also could confirm the silencing effect.

Next, Table 3 shows the effect of the case where both of the first target sound source 31 and the second target sound source 32 were driven and only the first additional sound source 41 was used for the silencing control.

TABLE 3

| | First Microphone | Second Microphone | Third Microphone |
|---|---|---|---|
| Before Control | 81.7 | 97.2 | 77.7 |
| During Control | 61.7 | 97.7 | 82.0 |

As shown in Table 3, the sound level detected by the first microphone 33 was reduced from 81.7 dB to 61.7 dB.

However, the sound level detected by the second microphone 34 was increased from 97.2 dB to 97.7 dB. Furthermore, the sound level detected by the third microphone 150 arranged at the position shown in FIG. 20 was increased from 77.7 dB to 82.0 dB. The experimenter also could not confirm the silencing effect.

It can be assumed in theory that the reason of the above result was that the sound radiated from the second target sound source 32 affected the microphone 33 to shift the phase and the amplitude from their theoretical values.

Next, Table 4 shows the effect of the case where both of the first target sound source 31 and the second target sound source 32 were driven, at first only the second additional sound source 42 and then both of the first additional sound source 41 and the second additional sound source 42 were used for the silencing control.

TABLE 4

| | First Microphone | Second Microphone | Third Microphone |
|---|---|---|---|
| Before Control | 81.7 | 97.2 | 78.0 |
| During Control by Second additional sound source | 72.0 | 82.5 | 77.6 |
| During Control by Both additional sound sources | 48.0 | 84.2 | 67.8 |

As shown in Table 4, because of the control by the second additional sound source 42, the sound level detected by the first microphone 33 was reduced from 81.7 dB to 72.0 dB. In addition, the sound level detected by the second microphone 34 was reduced from 97.2 dB to 82.5 dB. However, the sound level detected by the third microphone 150 arranged at the position shown in FIG. 20 was reduced only a little from 78.0 dB to 77.6 dB.

Then, after adding the control by the first additional sound source 41, the sound level detected by the first microphone 33 was further reduced to 48.0 dB. In addition, the sound level detected by the third microphone 150 was reduced to 67.8 dB. The sound level detected by the second microphone 34 was restrained to 84.2 dB. The experimenter also could confirm the silencing effect.

As described above, according to the seventh embodiment, since a silencing control is conducted in a two-stepped manner for a space including two target sound sources, the silencing control can achieve an excellent silencing effect.

What is claimed is:

1. A three-dimension active silencer, comprising:

a measuring unit configured to detect a signal relating to a sound radiated from a target sound source which is located in a closed box, a plurality of additional sound sources arranged around the target sound source, a microphone arranged at a predetermined position for detecting a sound power at the position, and a controller configured to control respective amplitudes of the additional sound sources which can be different from an amplitude of the target sound source and respective phases of the additional sound sources, based on the signal detected by the measuring unit, in such a manner that the microphone detects the lowest sound power, wherein the additional sound sources are arranged in such a manner that a position $x_p$ of the target sound source, respective relative positions $d_i$ (i=1, 2, . . . , N) of the N additional sound sources from the target sound source and a wave number k of the sound radiated from the target sound source substantially satisfy a relationship:

$$\frac{1}{N}\sum_{i=1}^{N}\cos k(x_p - d_i) - \cos k \cdot x_p \cong 0.$$

2. A three-dimension active silencer according to claim 1, wherein:

the controller has a digital controlling part including a controlling-coefficient calculator which calculates controlling coefficients and a controlling-coefficient processor which calculates a sum of products of the controlling coefficients and the signal, and the controlling coefficients are updated substantially every moment.

3. A three-dimension active silencer according to claim 1, wherein:

the controller has: an analogue controlling part including a first band-pass filter, a phase adjuster and an amplitude adjuster; and a sound-power monitoring part including a second band-pass filter, an AD/DA converter and a digital circuit.

4. A three-dimension active silencer according to claim 1, wherein:

the microphone is arranged in an area which is not in a node area of the sound radiated from the target sound source and which is not in node areas of sounds radiated from the additional sound sources.

* * * * *

UNITED STATES PATENT AND TRADEMARK OFFICE

CERTIFICATE OF CORRECTION

PATENT NO. : 6,901,147 B1
DATED : May 31, 2005
INVENTOR(S) : Enamito et al.

It is certified that error appears in the above-identified patent and that said Letters Patent is hereby corrected as shown below:

Title page,
Item [75], Inventors, should read
-- Akihiko Enamito, Kawasaki (JP)
Takuro Hayashi, Yokohama (JP)
Kunio Matsukura, Kawasaki (JP)
Satoshi Aoyagi, Yokohama (JP) --.

Signed and Sealed this

Twentieth Day of September, 2005

JON W. DUDAS
*Director of the United States Patent and Trademark Office*